United States Patent [19]

Dürr et al.

[11] Patent Number: 4,567,202

[45] Date of Patent: Jan. 28, 1986

[54] PHARMACEUTICAL AMITRIPTYLIN OXIDE PREPARATION AND PROCESS FOR ITS MANUFACTURE

[75] Inventors: Manfred Dürr, Pulheim-Dansweiler; Benedikt Gajdos, Cologne; Klaus-Dieter Gneuss, Cologne; Ekkehard Harhausen, Cologne; Jürgen Seidel, Pulheim, all of Fed. Rep. of Germany

[73] Assignee: A. Nattermann & Cie. GmbH, Fed. Rep. of Germany

[21] Appl. No.: 548,491

[22] Filed: Nov. 3, 1983

[30] Foreign Application Priority Data

Dec. 23, 1982 [DE] Fed. Rep. of Germany ....... 3247676

[51] Int. Cl.$^4$ ............................................ A61K 31/135
[52] U.S. Cl. ................................ 514/656; 260/501.17
[58] Field of Search ................... 424/330; 260/501.17; 514/656

[56] References Cited

PUBLICATIONS

Smith, Open–Chain Nitrogen Compounds, vol. 2, 1966, pp. 22 & 25.

*Primary Examiner*—Stanley J. Friedman
*Attorney, Agent, or Firm*—Keil & Weinkauf

[57] ABSTRACT

Stable pharmaceutical preparations comprising amitriptylin oxide dihydrate as an active substance and an organic acid from the group of hydroxy carboxylic acids, ketocarboxylic acids or amino acids as a stabilizer besides conventional pharmaceutical auxiliaries and carrier substances.

3 Claims, No Drawings

PHARMACEUTICAL AMITRIPTYLIN OXIDE PREPARATION AND PROCESS FOR ITS MANUFACTURE

BACKGROUND OF THE INVENTION AND PRIOR ART

The invention relates to galenic or pharmaceutical preparations for amitryptylin oxide dihydrate and processes for their manufacture.

Amitriptylin oxide dihydrate (3-(10,11-dihydro-5H-dibenzo- [a,d]-cycloheptene-5-ylidene)-N,N-dimethyl-1-propaneamine-N-oxide-dihydrate) has been available commercially for some time for the therapy of depressive conditions. However, the commercially available forms frequently suffer from inadequate stability, in particular in relatively warm climatic regions.

SUMMARY AND DETAILED DESCRIPTION OF THE INVENTION

It has now been found surprisingly that amitriptylin oxide dihydrate can be converted into pharmaceutical preparations which are suitable even in prolonged storage at relatively high temperatures, by the addition of an organic acid.

Suitable organic acids include hydroxycarboxylic acids as for example malic acid, racemic acid, tartaric acid, lactic acid, tatronic acid, mesoxalic acid dihydrate, glycolic acid, dihydroxyacetic acid, citric acid, glucuronic acid, oxalic acid or salicylic acid, ketocarboxylic acids such as for example α-ketoglutamic acid, mesoxalic acid, α-ketopropionic acid or acetone dicarboxylic acid, amino acids, such as for example, glutamic acid, glycine, glutamine, alanine, aspartic acid lysene, proline, histidine or leucine, particularly preferred being the hydroxycarboxylic acids, in particular citric acid.

In principle any toxicologically acceptable proton donors having physico-chemical properties enabling them to form stable preparations with amitriptyin oxide dihydrate may be used for the manufacture of stable amitriptylin oxide dihydrate-acid combination preparations.

For manufacturing the new pharmaceutical preparation, amitriptylin oxide dihydrate is dissolved jointly with the organic acid in a molar ratio ranging from 1:1 to 1:2 in water or an alcohol/water mixture. It is also possible for the amitriptylin oxide dihydrate and the organic acid to be dissolved separately in water or an alcohol/water mixture, followed by mixing of the solutions. Suitable alcohols are lower aliphatic alcohols, in particular isopropanol. The resulting solution is applied onto an auxiliary or carrier substance, the solvent is evaporated off and the resulting amitriptylin oxide dihydrate-acid combination preparation is pressed into tablets or is filled into capsules. The manufacture of the combination preparation may include moist granulation followed by drying, fluidised bed granulation or the spraying of the solution onto pellets.

Suitable auxiliaries or carrier substances include conventional pharmaceutical substances e.g. silica gels, calcium phosphates, calcium sulphate, monosaccharides, oligosaccharides and polysaccharides, saccharose, fructose, starch derived from rice, maize, potatoes, cellulose, fibrous substances, polymers etc.

The combination preparations may also be manufactured by mixing amitriptylin oxide dihydrate in crystalline form with conventional auxiliaries and/or carrier substances followed by granulation with a solution of the suitable acids and further processing.

The new combination preparations were subjected to a stability test (see table 1) wherein the preparations were subjected to an elevated temperature (the results of that test indicate a shelf life of at least 3 years for climatic zones I-IV).

TABLE 1

| Experiment number | Active substance/acid in grammes (in each case extended to 100 g with auxiliaries) | | | Preparation | Stability[1] |
|---|---|---|---|---|---|
| 1 | 100,0 | — | | P | 1 |
| 2 | 13,3 | — | | T | 2 |
| 3 | 9,2 | 7,5 | Malic acid | G | 15 |
| 4 | 9,2 | 7,5 | Malic acid | V | 10 |
| 5 | 9,4 | 4,3 | Tartaric acid | G | 15 |
| 6 | 9,4 | 4,3 | Tartaric acid | V | 7 |
| 7 | 8,8 | 11,2 | citric acid monohydrate | G | 40 |
| 8 | 8,8 | 11,2 | | V | 10 |
| 9 | 13,3 | 17,0 | | T | 38 |

[1]Stability: period in days for decomposing 10% of the active substance at 61° C.
P = powder
T = tablets
G = granulate: active substance and acids in solution granulated with an auxiliary in a moist condition
V = dry homogenate: the finely powdered components are mixed to homogenuity in a mortar or equivalent

EXAMPLE 1

800 g amitriptylin oxide dihydrate and 1020,80 g citric acid monohydrate are jointly dissolved in 1600 ml of an isopropanol/water mixture (1:1, v/v). This solution is added in a mixer (Diosna mixer) to a mixture of 3600 g Avicel PH (microcristaline cellulose) and 120 g Aerosil 200 (silicic acid). The moist granulate is dried thereafter (open tray or fluidised bed drying). The dry granulate is mixed in a mixer for the manufacture of a tabletting mix with 120 g Aerosil 200, 1699,20 g Avicel PH, 102,56 g Primogel (carboxymethycellulose) and 80 g magnesium stearate. Thereafter the tabletting mix is pressed into tablets by conventional methods.

EXAMPLE 2

800 g amitriptylin oxide dihydrate
2570,40 g Avicel PH 102
3200 g tricalciumphosphate
240 g Aerosil 200
are mixed together and are granulated in a fluidised bed granulator with a solution of 709,60 g α-ketoglutaric acid in 2000 ml ethanol/water (1:1, v/v). The fluidised bed granulate is then further mixed with 400 g Plastone XL and with 80 g magnesium stearate and the tabletting mixture is pressed into tablets in a conventional manner.

EXAMPLE 3

800 g amitriptylin oxide dihydrate
3200 g tricalcium phosphate
240 g Aerosil 200
are added together and granulated in a mixer with 1800 ml of a solution of 364,80 g glycine in water. The moist granulate is dried (open tray of fluidised bed drying). The dry granulate is subsequently mixed further with 2995,20 g lactose and 400 g talcum. The mixture is filled into hard gelatine capsules in a conventional manner.

EXAMPLE 4

800 g amitriptylin oxide dihydrate and
651,20 g DL-malic acid are dissolved in 4000 ml of ethanol (96%). 400 g Aerosil 200 are added to the solution. This mixture is spray-dried.

1851,20 g of this sprayed product are mixed with
4708,80 g dicalciumphosphate dihydrate
800 g Avicel PH 102
560 g Primogel and
80 g magnesium stearate
and the tabletting mixture is pressed into tablets in a conventional fashion.

We claim:

1. A pharmaceutical composition containing a stabilized amitriptylin oxide dihydrate, an effective amount of an organic acid stabilizer selected from the group consisting of malic acid, tartaric acid and citric acid, and a pharmaceutically acceptable auxiliary or carrier, said stabilized amitriptylin oxide dihydrate being formed by dissolving amitriptylin oxide dihydrate and the organic acid acid either jointly or separately in water or an alcohol-water mixture, applying the resultant solution containing the amitriptylin oxide dihydrate and said organic acid to the auxiliary or carrier and evaporating the solvent.

2. The composition of claim 1, wherein the organic acid is citric acid.

3. The composition of claim 1, wherein the solvent is a water-isopropanol mixture.

* * * * *